(12) United States Patent
Wiktor et al.

(10) Patent No.: US 10,350,344 B2
(45) Date of Patent: Jul. 16, 2019

(54) METHOD OF MONITORING AN EXTRACORPOREAL BLOOD TREATMENT AND APPARATUS FOR CARRYING OUT SAID METHOD

(71) Applicant: Fresenius Medical Care Deutschland GmbH, Bad Homburg (DE)

(72) Inventors: Christoph Wiktor, Gelnhausen (DE); Alexander Heide, Eppstein (DE); Arne Peters, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 436 days.

(21) Appl. No.: 14/903,644

(22) PCT Filed: Jul. 7, 2014

(86) PCT No.: PCT/EP2014/001858
§ 371 (c)(1),
(2) Date: Jan. 8, 2016

(87) PCT Pub. No.: WO2015/003795
PCT Pub. Date: Jan. 15, 2015

(65) Prior Publication Data
US 2016/0158433 A1    Jun. 9, 2016

(30) Foreign Application Priority Data

Jul. 9, 2013 (DE) .......... 10 2013 011 485
Jul. 26, 2013 (DE) .......... 10 2013 012 504

(51) Int. Cl.
*A61M 1/36* (2006.01)
*A61M 1/16* (2006.01)
(Continued)

(52) U.S. Cl.
CPC ........ *A61M 1/3656* (2014.02); *A61M 1/1603* (2014.02); *A61M 1/267* (2014.02);
(Continued)

(58) Field of Classification Search
CPC .. A61M 1/1005; A61M 1/1006; A61M 1/101; A61M 1/1086; A61M 1/1603; A61M 1/267; A61M 1/3693; A61M 1/3656; A61M 2205/15; A61M 2205/18; A61M 2205/3334; A61M 2230/005; A61M 2230/04; A61M 2230/30; A61M 2230/3341
See application file for complete search history.

(56) References Cited

U.S. PATENT DOCUMENTS

2004/0171977 A1* 9/2004 Paolini ............... A61M 1/3639
604/4.01
2011/0034814 A1* 2/2011 Kopperschmidt .. A61M 1/3639
600/485
(Continued)

FOREIGN PATENT DOCUMENTS

CN   102014984   4/2011
CN   102686252   9/2012
(Continued)

*Primary Examiner* — Benjamin J Klein
(74) *Attorney, Agent, or Firm* — Jacobson Holman, PLLC.

(57) ABSTRACT

The invention relates to a method of monitoring an extracorporeal blood treatment apparatus having an extracorporeal blood circuit and in particular a venous needle disconnection by means of pressure pulse measurement at the extracorporeal blood circuit. The invention further relates to an apparatus for carrying out a monitoring method and to a blood treatment apparatus which includes a corresponding monitoring apparatus.

25 Claims, 1 Drawing Sheet

(51) Int. Cl.
*A61M 1/26* (2006.01)
*A61M 1/10* (2006.01)
(52) U.S. Cl.
CPC ........... *A61M 1/3639* (2013.01); *A61M 1/101* (2013.01); *A61M 1/1005* (2014.02); *A61M 1/1006* (2014.02); *A61M 1/1086* (2013.01); *A61M 2205/15* (2013.01); *A61M 2205/18* (2013.01); *A61M 2205/3331* (2013.01); *A61M 2205/3334* (2013.01); *A61M 2205/3341* (2013.01); *A61M 2230/005* (2013.01); *A61M 2230/04* (2013.01); *A61M 2230/30* (2013.01)

(56) References Cited

U.S. PATENT DOCUMENTS

| | | | | |
|---|---|---|---|---|
| 2012/0330214 A1* | 12/2012 | Peters | ............... | A61M 1/3663 604/6.11 |
| 2013/0006128 A1* | 1/2013 | Olde | ................ | A61B 5/0215 600/486 |
| 2013/0204174 A1* | 8/2013 | Olde | ................ | A61M 1/3653 604/6.11 |

FOREIGN PATENT DOCUMENTS

| | | |
|---|---|---|
| DE | 102009060668 | 6/2011 |
| WO | WO 97/10013 | 3/1997 |
| WO | WO 03/002174 | 1/2003 |
| WO | WO 2012/175267 | 12/2012 |

\* cited by examiner

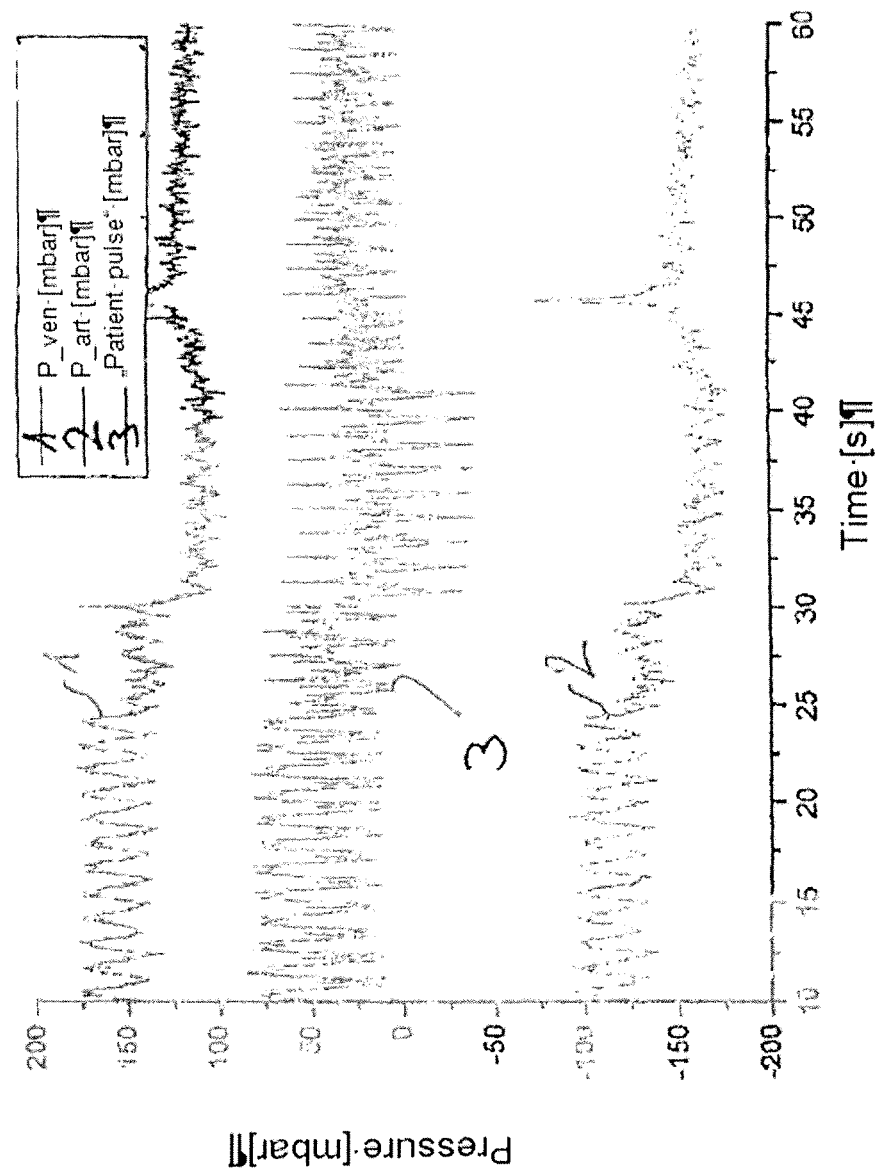

METHOD OF MONITORING AN EXTRACORPOREAL BLOOD TREATMENT AND APPARATUS FOR CARRYING OUT SAID METHOD

The invention relates to a method of monitoring an extracorporeal blood treatment apparatus in accordance with the preamble of claim 1 as well as to an apparatus for carrying out this method and to a corresponding blood treatment apparatus.

The present invention in particular deals with the problem of recognizing a venous needle disconnection by means of pressure pulse measurements at the extracorporeal blood circuit.

An unrecognized venous needle disconnection can result in the feared free-flow of blood from the venous needle into the environment if the pump cycle of the corresponding blood pump is not interrupted. If such a serious fault is not recognized immediately, the patient can bleed to death in a few minutes at typical blood flows of 200 ml/min to 300 ml/min. While a disconnection of the arterial needle is recognized immediately and reliably by the air bubble detectors always present within the blood treatment apparatus for preventing air embolisms due to the environmental air which is necessarily sucked in from the environment into the extracorporeal blood circuit, the reliable recognition of a venous needle disconnection still represents a technical challenge despite the many known solution approaches. In the known methods and apparatus, false alarms namely frequently occur due to incorrectly interpreted measured values so that generally unwanted alarm situations very frequently result and due to these a switching off of the extracorporeal blood treatment apparatus even though no venous needle disconnection is present.

It is already known from WO 971 00 13 A1 to monitor the integrity of the extracorporeal blood circuit with reference to the propagation of pressure pulses in the extracorporeal blood circuit. It is proposed in this respect that the pressure pulses to be monitored can be generated either by means of a pressure wave generator, e.g. the blood pump itself, or pressure pulses from the heart of the patient propagated in the extracorporeal blood circuit can alternatively be evaluated. Only peristaltic blood pumps, i.e. occluding blood pumps, are disclosed in WO 97/10013 A1, with it being pointed out here that these occluding blood pumps are blood pumps typically used for hemodialysis. The peristaltic blood pumps, also called roller pumps, occlude a pump hose segment of the extracorporeal blood circuit with the rollers of their rotor and thus generate a pulsating flow with strong pressure pulses. These pressure pulses of the occluding blood pump thus form strong signals such that all other pressure signals in the extracorporeal blood circuit are drowned out as noise in an unfiltered pressure signal evaluation. This has the result that an evaluation of the pressure pulses from the heart of the patient cause very complex and/or expensive evaluation methods, on the one hand, and are nevertheless prone to error, on the other hand.

Extracorporeal blood circuits having centrifugal pumps, and here in particular having impeller pumps, are known outside the field of hemodialysis. Such systems are used, for example, in heart surgery.

An apparatus and a method for recognizing a venous needle disconnection at an extracorporeal blood circuit having an impeller pump are furthermore described in DE 10 2009 060 668 A1. Here, the shallow characteristic of such an impeller pump at a constant speed is used to recognize a very small pressure variation due to a venous needle disconnection on the basis of the resulting, reliably measurable variation in the conveyed blood flow. The recognition is utilized in this respect that impeller pumps are not occluding and allow pressure pulses to pass.

Impeller blood pumps are typically components of a disposable or of a blood hose kit, in particular also of a blood cassette. The impeller of such impeller blood pumps is magnetically supported as a rule so that it is driven contactlessly. The impeller of the impeller blood pump therefore only comes into contact involving friction with the conveyed blood. The support of the impeller can also be a combination of magnetic, hydraulic and/or mechanical support.

It is the object of the present invention to further develop the already known process of monitoring an extracorporeal blood treatment apparatus such that a venous needle disconnection is reliably recognized in a simple manner.

This object is achieved in accordance with the invention by a method in accordance with claim 1.

This method in accordance with the invention serves the monitoring of an extracorporeal blood treatment apparatus having an extracorporeal blood circuit which has an arterial blood line having an arterial patient port and a venous blood line having a venous patient port, with an impeller pump or a centrifugal pump being arranged in the arterial or venous blood line for conveying blood in the extracorporeal blood circuit. The method in accordance with the invention has the following steps in detail:

measuring at least one first pressure amplitude and/or one first course of a pressure amplitude as a reference value at at least one pressure measurement site of the extracorporeal blood circuit, calculating at least one limit pressure value on the basis of the first pressure amplitude recorded as the reference value and/or fixing a reference pressure course on the basis of the first course of the pressure amplitude, measuring at least one second pressure amplitude and/or a second course of the pressure amplitude at the at least one pressure measurement site of the extracorporeal blood circuit.

comparing the second pressure amplitude with the at least one limit pressure value and/or comparing the second course of the pressure amplitude with the reference pressure course and stopping or substantially reducing the speed of the blood pump and/or closing the venous hose clamp if an unpermitted difference from the reference value and/or from the reference pressure course is determined.

Advantageous embodiments of the invention result from the dependent claims following on from the main claim.

Accordingly, on a determination of an unpermitted difference, an acoustic and/or optical and/or tactile alarm can be output to allow a fast intervention.

In specific embodiments, a substantial throttling of the blood pump, for example by lowering the speed to less than 100 r.p.m., for example approximately 500 r.p.m., can be provided instead of the stopping of the blood pump.

In accordance with another advantageous embodiment of the invention, the impeller blood pump or centrifugal blood pump can be controlled such that its speed is constant. In specific embodiments, the speed of the impeller blood pump or centrifugal blood pump is kept constant at least during the measurement of the pressure amplitudes.

It is furthermore of particular advantage that the pressure pulses of the heart of the patient are recorded as pressures values to be processed in the method in accordance with the invention.

In accordance with a further aspect of the invention, an apparatus for carrying out the aforesaid method having a monitoring apparatus is claimed, wherein the monitoring apparatus has a control and processing unit which is configured such that, on a difference of the currently measured pressure amplitude from the reference value and/or on a difference of the current pressure course, a conclusion is drawn of a disturbance of the patient access, in particular this leads to the detection and determination of a venous needle disconnection. The monitoring apparatus can in particular be an external one.

The apparatus advantageously has at least one pressure sensor.

One pressure sensor is generally sufficient which in this respect, like the impeller pump or the centrifugal pump, is connected to the control and processing unit.

In accordance with a further advantageous embodiment of the invention, the apparatus has the drive unit for the impeller blood pump or for the centrifugal blood pump.

Finally, the present invention also comprises a blood treatment apparatus which is configured for carrying out a hemodialysis and/or hemofiltration and/or hemodiafiltration and which has a monitoring apparatus with a control which is programmed and configured to recognize an arterial and/or venous needle disconnection using the above-described method.

The present invention further comprises a blood treatment apparatus to be used with an extracorporeal blood circuit having an arterial blood line with an arterial patient port and a venous blood line with a venous patient port, wherein an impeller or centrifugal pump for conveying blood in the extracorporeal blood circuit is located in the arterial or venous blood line, with a control unit, that is programmed and configured to detect needle disconnections, wherein the control unit is programmed to evaluate the pressure signals of at least one pressure sensor. The control unit is implemented such that the amplitudes of the pressure pulses of the patient's heart measured in the extracorporeal blood circuit are compared to at least one threshold value or reference course.

The blood treatment apparatus may be implemented in a way that allows pre-determining the threshold value or reference course based on an initial reading during a disturbance-free operation of the extracorporeal blood circuit.

The control and processing unit is preferably programmed to compare the threshold value or reference course previously saved in a data storage to the current reading, wherein the occurrence of inadmissible deviations from the measured amplitude of the pressure pulses from the patient's heart will be regarded as a defective vascular access.

The method described above and the apparatus according to the present invention or blood treatment apparatus may be implemented as follows:

The amplitude of the pressure pulses of the patient's heart is preferably calculated by deducting the local minima from the local maxima of the pressure pulse curve. The control unit may thereby in particular have a minimum and maximum value acquisition unit and calculate the amplitude, which is used for the comparison with a threshold value, using the difference between consecutive minimum and maximum values.

Furthermore the pressure signals of the at least one pressure sensor may be a sum signal of the pressure impulses of the patient's heart that are transmitted to the pressure sensor via the arterial and the venous patient port if there is a correct connection.

Furthermore the method and/or the control unit of the apparatus or blood treatment apparatus according to the present invention may comprise the provision that even a deviation of the amplitude of the pressure pulse of less than 90% and preferably less than 75% as compared to the amplitude of the pressure pulses in case of a correct connection will be regarded as a disconnection. Hence it is taken into account that if there is a disconnection only in the arterial access or only in the venous access, signals from the heart still reach the via the other to the pressure sensor and that therefore the amplitude in the sum signal according to the present invention will not drop to zero despite the occurrence of a disconnection.

In particular a change of the signal may be regarded as a disconnection even though the signal still receives pressure pulses from the patient's heart whose amplitude amounts to 10% and preferably 25% of an amplitude representing a correct connection.

According to the present invention the impeller or centrifugal pump may furthermore be located between the pressure sensor and the venous patient port, and/or wherein the pressure sensor is located in the venous drip chamber.

It may furthermore be part of the present invention to detect both a venous and an arterial disconnection by comparing the amplitudes of the pressure pulses of the patient's heart measured in the extracorporeal blood circuit to at least one threshold value or reference course, and/or wherein both a venous and an arterial disconnection is detected by evaluating the pressure signals of a single pressure sensor.

According to the present invention the pressure signals furthermore are not separated into frequency components and/or the frequency components are not suppressed or filtered, i.e. the comparison to a threshold value and/or a reference course according to the present invention is based on a signal which has not been processed in this manner.

Furthermore a needle disconnection can be detected without taking into account the form, frequency and/or absolute height of the measured signal.

It may furthermore be part of the present invention to detect a needle disconnection at the latest after 5, preferably after 3, even more preferably after 1.5 periods of the pressure pulses of the patient's heart and/or after an inadmissible change of the pressure amplitude lasting longer than 5, preferably longer than 3, even more preferably longer than 1.5 periods of the pressure pulses of the patient's heart be regarded as a needle disconnection and/or wherein an inadmissible change in the pressure amplitude lasting longer than 5, preferably longer than 3, even more preferably longer than 1.5 seconds will be regarded as a needle disconnection.

The method and procedure described above are preferably performed automatically by the control of the blood treatment apparatus according to the present invention.

The control and processing unit may therein be configured and/or programmed to perform one of the methods described above, especially automatically. The control and processing unit may therein operate as described above with reference to the method.

Further features, details and advantages of the invention will be explained in the following with reference to an embodiment and to a FIGURE.

The only FIGURE shows the measured pressure course of the venous and arterial pressure course at an extracorporeal blood circuit operated using an impeller blood pump while displaying the event of a venous needle disconnection.

The method in accordance with the present invention is realized in an extracorporeal blood treatment apparatus in accordance with the embodiment shown here. The extracorporeal blood treatment apparatus can, for example, be a known hemodialysis apparatus such as is described in DE 10 2009 060 668 A1, for example.

Reference is made to the description of the hemodialysis apparatus shown there by way of example as a typical blood treatment apparatus for the use of the present invention. The extracorporeal blood treatment apparatus of the invention in particular has a control and processing unit and, at the machine side, a drive for an impeller blood pump. The impeller blood pump comprises a housing with impeller and is preferably a component of the extracorporeal blood hose kit which is particularly advantageously designed as a disposable blood cassette, with the extracorporeal blood hose kit being configured for coupling to the extracorporeal blood treatment apparatus.

The blood treatment machine furthermore has at least one pressure sensor which is configured for coupling to a pressure measurement site of the extracorporeal blood hose kit.

The pressure sensor and the impeller blood pump are connected to the control and processing unit. A wireless transfer to the disposable blood hose kit can advantageously be provided as a connection to the control and processing unit. Such wireless connections are known from the application of integrated RFID pressure sensors with a disposable blood hose kit.

The control and processing unit has a data memory in which a computer program is stored. The program code of the computer program is programmed to evaluate the pressure signals of the at least one pressure sensor. Here in particular the amplitudes of the pressure pulses from the heart of the patient measured at the extracorporeal blood circuit are compared with at least one threshold value or the reference course. The threshold value or reference course is previously determined on the basis of an initial measurement in the extracorporeal blood circuit during a failure-free operation. In this case, the control and processing unit is designed so that the threshold value or reference course, which was previously stored in the data memory, is compared with the current measured values. On the occurrence of an unpermitted difference of the measured amplitude of the pressure pulses from the heart of the patient, a conclusion is drawn of a defective vessel access, in the present case, of a venous needle disconnection.

It is no longer necessary within the framework of the present invention to provide at least one arterial pressure measurement site and one venous pressure measurement site at the extracorporeal blood hose kit. It is fully sufficient for the carrying out of the invention to arrange at least one single pressure sensor at the extracorporeal blood hose kit since, in the case of an arterial and/or venous needle disconnection, the amplitude of the measured heart pressure pulse varies everywhere in the extracorporeal blood circuit. The measured signal is a sum signal of the signals created by the heart and transmitted to the extracorporeal blood circuit via the venous and arterial port. In case of a disconnection of only the arterial needle or only the venous needle the measured amplitude of the pressure pulses of the patient's heart would therefore change without dropping to zero. In the case of a disconnection of the arterial needle and of the venous needle, the measured amplitude of the pressure pulses from the heart of the patient would drop to zero. The reliability of the recognition of a needle disconnection in this respect naturally decisively depends on the selected threshold values or reference courses.

A typical signal course for a needle disconnection to be detected can be explained with reference to the FIGURE.

Three curves are drawn here. The upper curve shows the venous pressure course, the lower curve the arterial pressure course. These pressure courses are measured in an extracorporeal blood circuit which is operated by means of an impeller blood pump. The course of the pressure pulse waves of the patient caused by cardiac contraction is shown in the middle. It becomes clear that the amplitude course of the measured venous and arterial pressure course falls greatly after the venous needle disconnection, i.e. at a time t=25 sec. This variation can be detected as a defect, i.e. as a needle disconnection. The course of the pressure pulse waves of the patient caused by the cardiac contraction determined in parallel in accordance with the middle curve in the FIGURE has been measured in a different manner and is only shown in the same graph for comparison here. This course is usually not recorded in the apparatus in accordance with the invention. The comparison with this course, however, shows that the pulses of the venous and arterial pressure courses extend synchronously with those of the heart pulses and that therefore no substantial other interference signals are present. This is only possible due to the use of the impeller blood pump or of the centrifugal blood pump.

In the framework of the present invention the following measuring principle is used preferably:

The pressure pulse curve of the heart pulses is measured in the extracorporeal blood circuit (EBC). Since the system according to the present invention does not require any occluding components, and especially no peristaltic pumps, it is intended as an open system, i.e. the pressure pulses of the heart are transmitted to the EBC via both patient ports and are superimposed there. Hence a sum signal is created which is not interfered with by (pressure) actuators of the EBC. Thanks to the system's open concept the pressure sensor may be located at any position in the system and may for example a pressure sensor arranged in the venous drip chamber may be used.

After a disconnection of one of the two patient lines the pressure sensor in the EBC will receive a different signal, which no longer constitutes a sum signal. As a consequence the pressure amplitude changes (half the difference of the local minima and maxima of the pressure pulse curve) significantly. In the embodiment shown in FIG. 1 this value changes from about 40 mbar to about 20 mbar, i.e. by a factor of about 2, during a venous disconnection occurring after about 25 seconds.

Furthermore, contrary to a peristaltic pump, an impeller or a centrifugal pump does not create its own pressure pulses. Therefore, the sum signal of the signals coming from the patient's heart can be evaluated directly because of the lack of interfering signals from the EBC. According to the present invention no post-processing of the signal in the sense of a transformation into the frequency domain and of filtering unwanted signal components is required. The system does not require a Fourier transformation, hence there is no need for a continually recurring signal. A venous needle disconnection may basically already be detected after 1.5 periods according to the present invention.

Furthermore the detection does not depend on the absolute change of the signal as long as local minima and maxima can be detected. Changes in the frequency, for example in the case of a fluctuating heart rate, do not influence the system either.

It also does not matter whether there is a venous or an arterial needle disconnection. Both events can be detected using the same method.

The invention claimed is:

1. In a method of monitoring extracorporeal blood treatment of a patient using an apparatus having an extracorporeal blood circuit containing an arterial blood line having an arterial patient port with an arterial needle connecting to the patient, a venous blood line having a venous patient port with a venous needle connecting to the patient, and a blood pump arranged in the arterial or venous blood line for conveying blood in the extracorporeal blood circuit, the improvement characterized in that the blood pump is an impeller pump or a centrifugal pump, and the apparatus further has a controller programmed and configured to recognize disconnection of one or both of the arterial and venous needles by performing the method having the following steps:

measuring at least one first pressure pulse amplitude and/or one first course of a pressure pulse amplitude for recording as a reference value by at least one pressure sensor at at least one pressure measurement site of the extracorporeal blood circuit, calculating at least one limit pressure value on the basis of the first pressure pulse amplitude recorded as the reference value and/or fixing a reference pressure course on the basis of the first course of the pressure pulse amplitude, measuring at least one second pressure pulse amplitude and/or a second course of the pressure pulse amplitude by the at least one pressure sensor at the at least one pressure measurement site of the extracorporeal blood circuit, comparing the second pressure pulse amplitude with the at least one limit pressure value and/or comparing the second course of the pressure pulse amplitude with the reference pressure course, and stopping or reducing the speed of the blood pump and/or closing a venous hose clamp if an unpermitted difference from the reference value and/or from the reference pressure course is determined, wherein there is no disconnection when the pressure pulse measured by the at least one pressure sensor is a sum signal consisting of pressure pulses of the patient's heart transmitted to the pressure sensor via the arterial and venous patient ports.

2. The method in accordance with claim 1, characterized in that, on detecting an unpermitted difference, an acoustic and/or optical and/or tactile alarm is output.

3. The method in accordance with claim 1, characterized in that the impeller blood pump or the centrifugal blood pump is controlled such that its speed is constant.

4. The method in accordance with claim 1, characterized in that the pressure pulses of the heart are recorded.

5. The method according to claim 1, wherein the amplitude of the pressure pulses is calculated by deducting the local minima from the local maxima of the pressure pulse curve.

6. The method according to claim 1, wherein even a deviation of the amplitude of the pressure pulses of less than 90% as compared to the amplitude of the pressure pulses in case of a correct connection will be regarded as a disconnection.

7. The method according to claim 1, wherein the impeller or centrifugal pump is located between the pressure sensor and the venous patient port, and/or wherein the pressure sensor is located in the venous drip chamber.

8. The method according to claim 1, wherein both a venous and an arterial disconnection are detected by comparing the amplitudes of the pressure pulses of the patient's heart measured in the extracorporeal blood circuit to at least one threshold value or reference course, and/or wherein both a venous and an arterial disconnection are detected by evaluating the pressure signals of a single pressure sensor.

9. The method according to claim 1, wherein the pressure signals are not separated into frequency components and/or frequency components are not suppressed or filtered and/or wherein a needle disconnection is detected at the latest after 5 periods of the pressure pulses of the patient's heart and/or an inadmissible change of the pressure amplitude lasting longer than 5 periods of the pressure pulses of the patient's heart will be regarded as a needle disconnection and/or wherein an inadmissible change in the pressure amplitude lasting longer than 5 seconds will be regarded as a needle disconnection.

10. The method of claim 1, wherein the extracorporeal blood circuit contains no peristaltic pump.

11. An apparatus useful for monitoring an extracorporeal blood circuit containing an arterial blood line having an arterial patient port with an arterial needle connecting to the patient, a venous blood line having a venous patient port with a venous needle connecting to the patient, and a blood pump arranged in the arterial or venous blood line for conveying blood in the extracorporeal blood circuit, characterized in that the apparatus has a control and processing unit programmed and configured to perform a method recognizing disconnection of one or both of the arterial and venous needles and comprising the steps of:

measuring at least one first pressure pulse amplitude and/or one first course of a pressure pulse amplitude for recording as a reference value by at least one pressure sensor at at least one pressure measurement site of the extracorporeal blood circuit, calculating at least one limit pressure value on the basis of the first pressure pulse amplitude recorded as the reference value and/or fixing a reference pressure course on the basis of the first course of the pressure pulse amplitude, measuring at least one second pressure pulse amplitude and/or a second course of the pressure pulse amplitude by the at least one pressure sensor at the at least one pressure measurement site of the extracorporeal blood circuit, comparing the second pressure pulse amplitude with the at least one limit pressure value and/or comparing the second course of the pressure pulse amplitude with the reference pressure course, and stopping or reducing the speed of the blood pump and/or closing a venous hose clamp if an unpermitted difference from the reference value and/or from the reference pressure course is determine, wherein there is no disconnection when the pressure pulse measured by the pressure sensor is a sum signal consisting of pressure pulses of the patient's heart transmitted to the pressure sensor via the arterial and venous patient port.

12. The apparatus in accordance with claim 11, further having at least one pressure sensor.

13. The apparatus in accordance with claim 11, further having drive unit for the blood pump.

14. The apparatus according to claim 11, wherein the amplitude of the pressure pulses is calculated by deducting the local minima from the local maxima of the pressure pulse curve.

15. The apparatus according to claim 11, wherein even a deviation of the amplitude of the pressure pulses of less than 90% as compared to the amplitude of the pressure pulses in case of a correct connection will be regarded as a disconnection.

16. The apparatus according to claim 11, wherein the impeller or centrifugal pump is located between the pressure sensor and the venous patient port, and/or wherein the pressure sensor is located in the venous drip chamber.

17. The apparatus according to claim 11, wherein both a venous and an arterial disconnection are detected by comparing the amplitudes of the pressure pulses of the patient's heart measured in the extracorporeal blood circuit to at least one threshold value or reference course, and/or wherein both a venous and arterial disconnection are detected by evaluation the pressure signal of a single pressure sensor.

18. The apparatus according to claim 11, wherein the pressure signals are not separated into frequency components and/or frequency components are not suppressed or filtered and/or wherein a needle disconnection is detected at the latest after 5 periods of the pressure pulses of the patient's heart and/or an inadmissible change of the pressure amplitude lasting longer than 5 periods of the pressure pulses of the patient's heart will be regarded as a needle disconnection and/or wherein an inadmissible change in the pressure amplitude lasting longer than 5 seconds will be regarded as a needle disconnection.

19. A blood treatment apparatus to be used with an extracorporeal blood circuit having an arterial blood line having an arterial patient port and a venous blood line having a venous patient port, with an impeller or centrifugal pump being arranged in the arterial or venous blood line for conveying blood in the extracorporeal blood circuit with a controller that is programmed and configured to detect a needle disconnection, wherein the controller is programmed to evaluate the pressure signals of at least one pressure sensor,
characterized in that
the amplitudes of the pressure pulses of the patient's heart measured in the extracorporeal blood circuit are compared to at least one reference value or reference course, wherein the pressure signals of the at least one pressure sensor are a sum signal consisting of the pressure pulses of the patient's heart which are transmitted to the pressure sensor via the arterial and venous patient port if the connection is correct and wherein even a deviation of the amplitude of the pressure pulses of less than 90% as compared to the amplitude of the pressure pulses in case of a correct connection will be regarded as a disconnection.

20. A blood treatment apparatus according to claim 19, wherein the reference value or reference course is determined in advance based on an initial reading during an interference-free operation of the extracorporeal blood circuit, and/or wherein the control and accounting unit is programmed to compare the threshold value or reference course previously saved in a data storage to the current reading, wherein the occurrence of inadmissible deviations from the measured amplitude of the pressure pulses from the patient's heart will be regarded as a defective vascular access.

21. The apparatus according to claim 19, wherein the amplitude of the pressure pulses is calculated by deducting the local minima from the local maxima of the pressure pulse curve.

22. The apparatus according to claim 19, wherein even a deviation of the amplitude of the pressure pulses of less than 75% as compared to the amplitude of the pressure pulses in case of a correct connection will be regarded as a disconnection.

23. The apparatus according to claim 19, wherein the impeller or centrifugal pump is located between the pressure sensor and the venous patient port, and/or wherein the pressure sensor is located in the venous drip chamber.

24. The apparatus according to claim 19, wherein both a venous and an arterial disconnection are detected by comparing the amplitudes of the pressure pulses of the patient's heart measured in the extracorporeal blood circuit to at least one threshold value or reference course, and/or wherein both a venous and an arterial are detected by evaluating the pressure signal of a single pressure sensor.

25. The apparatus according to claim 19, wherein the pressure single are not separated into frequency components and/or frequency components are not suppressed or filters and/or wherein a needle disconnection is detected at the latest after 5 periods of the pressure pulses of the patient's heart and/or an inadmissible change of the pressure amplitude lasting longer than 5 periods of the pressure pulses of the patient's heart will be regarded as a needle disconnection and/or wherein an inadmissible change in the pressure amplitude lasting longer than 5 seconds will be regarded as a needle disconnection.

\* \* \* \* \*